(12) United States Patent
Hwang et al.

(10) Patent No.: US 12,204,179 B2
(45) Date of Patent: Jan. 21, 2025

(54) WEARABLE MODEL EYE APPARATUS (71) Applicant: INDUSTRY-ACADEMIC COOPERATION FOUNDATION GYEONGSANG NATIONAL UNIVERSITY, Jinju-si (KR)

(72) Inventors: Hosik Hwang, Seoul (KR); Seongjae Kim, Jinju-si (KR)

(73) Assignee: Industry-Academic Cooperation Foundation Gyeongsang National University, Jinju-si (KR)

( * ) Notice: Subject to any disclaimer, the term of this patent is extended or adjusted under 35 U.S.C. 154(b) by 623 days.

(21) Appl. No.: 17/594,833

(22) PCT Filed: Apr. 29, 2020

(86) PCT No.: PCT/KR2020/005684
§ 371 (c)(1),
(2) Date: Oct. 29, 2021

(87) PCT Pub. No.: WO2020/222534
PCT Pub. Date: Nov. 5, 2020

(65) Prior Publication Data
US 2022/0197057 A1 Jun. 23, 2022

(30) Foreign Application Priority Data
Apr. 30, 2019 (KR) .......................... 10-2019-0050201

(51) Int. Cl.
*G02C 7/04* (2006.01)
*A61B 3/00* (2006.01)
(52) U.S. Cl.
CPC ................ *G02C 7/047* (2013.01); *A61B 3/00* (2013.01)

(58) Field of Classification Search
CPC .......... G02C 7/047; G02C 7/088; A61B 3/00; A61B 3/0025; A61F 2/16; G02B 27/0172; G02B 3/0037; G02B 27/0176
(Continued)

(56) References Cited

U.S. PATENT DOCUMENTS 5,652,640 A 7/1997 Schneider et al.
6,358,280 B1 * 3/2002 Herrick ................. A61F 2/1613
623/6.34
(Continued)

FOREIGN PATENT DOCUMENTS

JP 2005521898 A * 7/2005
JP 2012068551 A 4/2012
(Continued)

OTHER PUBLICATIONS

English Search Report in International Application No. PCT/KR2020/005684—in 2 pages (Aug. 18, 2020).
(Continued)

*Primary Examiner* — Mohammed A Hasan
(74) *Attorney, Agent, or Firm* — Knobbe, Martens, Olson, & Bear, LLP (57) ABSTRACT Disclosed is a model eye apparatus by which patients can wear an intraocular lens in reality before a surgery and experience an image that the patients will actually see after the surgery. A wearable model eye apparatus according to the present invention comprises: a plurality of guide members arranged in parallel; an intraocular lens module which is installed to be movable forward or backward by guidance of the plurality of guide members and has an intraocular lens installed therein; and a minus lens module which is installed in front of the intraocular lens module to be movable forward or backward by guidance of the plurality of guide members and has a minus lens disposed therein.

14 Claims, 8 Drawing Sheets

(58) Field of Classification Search
USPC .......................................................... 351/205
See application file for complete search history.

(56) References Cited

U.S. PATENT DOCUMENTS

| | | | |
|---|---|---|---|
| 9,211,061 | B2 | 12/2015 | Kasthurirangan et al. |
| 2006/0119794 | A1* | 6/2006 | Hillis ........................ G02B 3/14 |
| | | | 351/205 |
| 2009/0198326 | A1* | 8/2009 | Zhou ...................... A61F 2/1613 |
| | | | 623/6.34 |
| 2010/0110379 | A1* | 5/2010 | Zhou ...................... A61B 3/103 |
| | | | 351/205 |
| 2011/0080562 | A1* | 4/2011 | Iizuka ................... A61B 3/0025 |
| | | | 351/233 |

FOREIGN PATENT DOCUMENTS

| | | |
|---|---|---|
| KR | 20180013591 A | 2/2018 |
| KR | 101893521 B1 | 8/2018 |
| WO | 93/01765 | 2/1993 |

OTHER PUBLICATIONS

Extended European Search Report dated Dec. 16, 2022 of the corresponding EP Application No. 20799182.9.

* cited by examiner

WEARABLE MODEL EYE APPARATUS

TECHNICAL FIELD

The present invention relates to a model eye apparatus by which patients can wear an intraocular lens (IOL) in reality before a surgery and experience an image that the patients will actually see after the surgery.

BACKGROUND

In general, during cataract surgery, the cloudy lens is removed and an intraocular lens (IOL) is inserted. Recently, not only general monofocal intraocular lens but also multifocal intraocular lens have been widely used. When a multifocal intraocular lens is inserted, it is said that both distant and near objects can be seen clearly.

However, there is no way to objectively evaluate how a patient with a multifocal intraocular lens actually sees the world. There is a method of inserting a multifocal intraocular lens into a model eye in an optical laboratory and testing it using a standardized visual target, but since this is different from the actual environment, there is a problem in that it is difficult to deliver the simulated postsurgical information to the patient.

SUMMARY

Technical Tasks

The present invention is directed to providing a model eye apparatus through which a patient can experience postsurgical vision in advance by wearing the apparatus, wherein an intraocular lens suitable for the patient among various intraocular lenses can be selected and assembled.

Technical Solution

The present invention may include a plurality of guide members arranged in parallel; an intraocular lens module which is installed to be movable forward or backward by guidance of the plurality of guide members and has an intraocular lens installed therein; and a minus lens module which is installed in front of the intraocular lens module to be movable forward or backward by guidance of the plurality of guide members and has a minus lens disposed therein.

In this case, the present invention may further include a frame fixedly installed at the rear end of the plurality of guide members to support the plurality of guide members in a parallel state.

In this case, the present invention may further include a wearing part connected to the frame such that the intraocular lens module and the minus lens module are arranged in a line in front of a wearer's eye to be worn.

In this case, a through-hole through which the plurality of guide members pass is formed in the main body of the intraocular lens module and the minus lens module so that the intraocular lens module and the minus lens module move forward or backward in the same direction.

In this case, the bodies of the intraocular lens module and the minus lens module may be made in a rectangular parallelepiped shape.

In this case, the minus lens module and the intraocular lens module may be disposed to be in contact with each other.

In this case, the absolute value of the focal length of the intraocular lens module may be greater than the absolute value of the focal length of the minus lens.

In this case, the intraocular lens may be a multifocal intraocular lens.

In this case, a cushion member for protecting the wearer may be provided on the rear surface of the frame.

In this case, the wearing part may be a pair of glass frames having one end connected to the frame and the other end being able to be hung on the wearer's ear.

In this case, the wearing part may be a band having both ends fixed to the frame so as to pass around the wearer's head.

In this case, the wearing part may be made in the form of a helmet, and the frame may be fixed to the front of the helmet.

In this case, the intraocular lens module may include a main body having a through-hole formed therein; an intraocular lens mounted in the horizontal direction so as to be fixed inside the through-hole of the main body; a window members fixed at upper and lower ends of the through-hole of the main body so that the inside of the through-hole of the main body is sealed, and made of a transparent material; a pair of ring-shaped fixing adapters fixed to an assembling jaw formed inside the main body, wherein the intraocular lens is positioned fixedly between the pair of fixing adapters; and an aqueous solution filled inside the through-hole.

In this case, the intraocular lens module and the minus lens module may be detachably attached to the plurality of guide members so that they can be replaced with other modules.

In this case, the present invention may further include a plurality of replaceable intraocular lens modules in the guide member, wherein the size of the central holes formed in the fixing adapters of the plurality of intraocular lens modules is different from each other.

Effects

As described above, according to the present invention, there are the following effects.

(1) The present invention provides the effect of visually showing the visual images of various environments to be actually seen to the patient after surgery while moving with actually wearing the apparatus.

(2) The present invention can be applied to various visual test equipment by modularizing the intraocular lens to improve portability.

DETAILED DESCRIPTION OF THE EMBODIMENTS

Hereinafter, exemplary embodiments of the present invention will be described in detail so that those of ordinary skill in the art can readily implement the present invention with reference to the accompanying drawings. The present invention may be embodied in many different forms and are not limited to the embodiments set forth herein. In the drawings, parts unrelated to the description are omitted for clarity. Throughout the specification, like reference numerals denote like elements.

It is understood that the terms "comprise" or "have" when used in this specification, are intended to specify the presence of stated features, integers, steps, operations, members, components and/or a combination thereof but not preclude the possibility of the presence or addition of one or more other features, integers, steps, operations, members, components, or a combination thereof. In addition, it will be understood that when an element such as a layer, film, region, or substrate is referred to as being "on" another element, it can be "directly on" the other element or intervening elements may also be present. Conversely, it will be understood that when an element such as a layer, film, region, or substrate is referred to as being "below" another element, it can be "directly below" the other element or intervening elements may also be present.

Hereinafter, a model eye apparatus 1 according to an embodiment of the present invention will be described in more detail with reference to the drawings.

Figure 1:
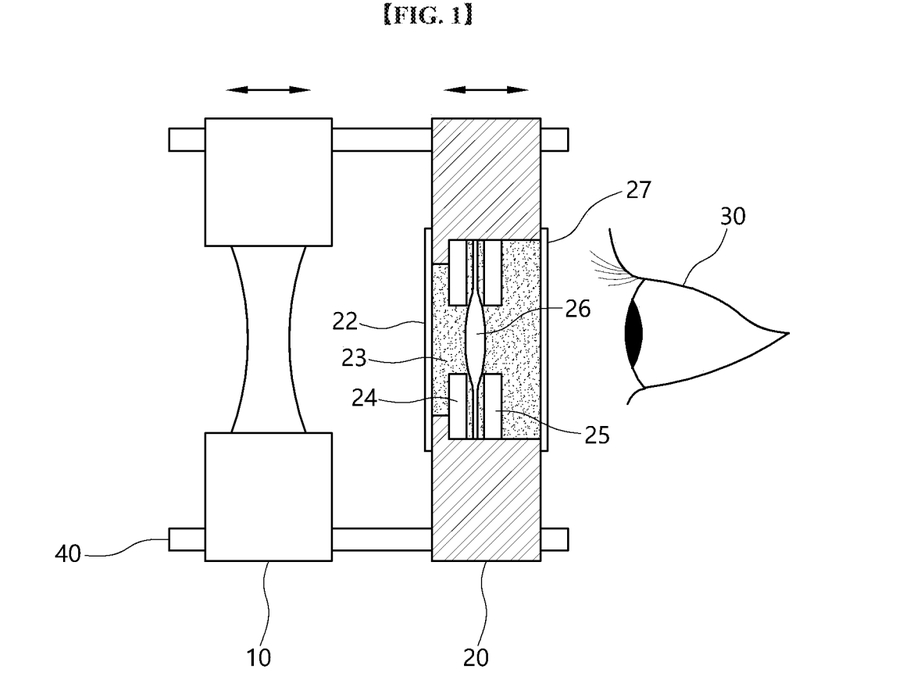
FIG. 1 is a partial configuration view of a wearable model eye apparatus according to an exemplary embodiment of the present invention.
Figure 2:
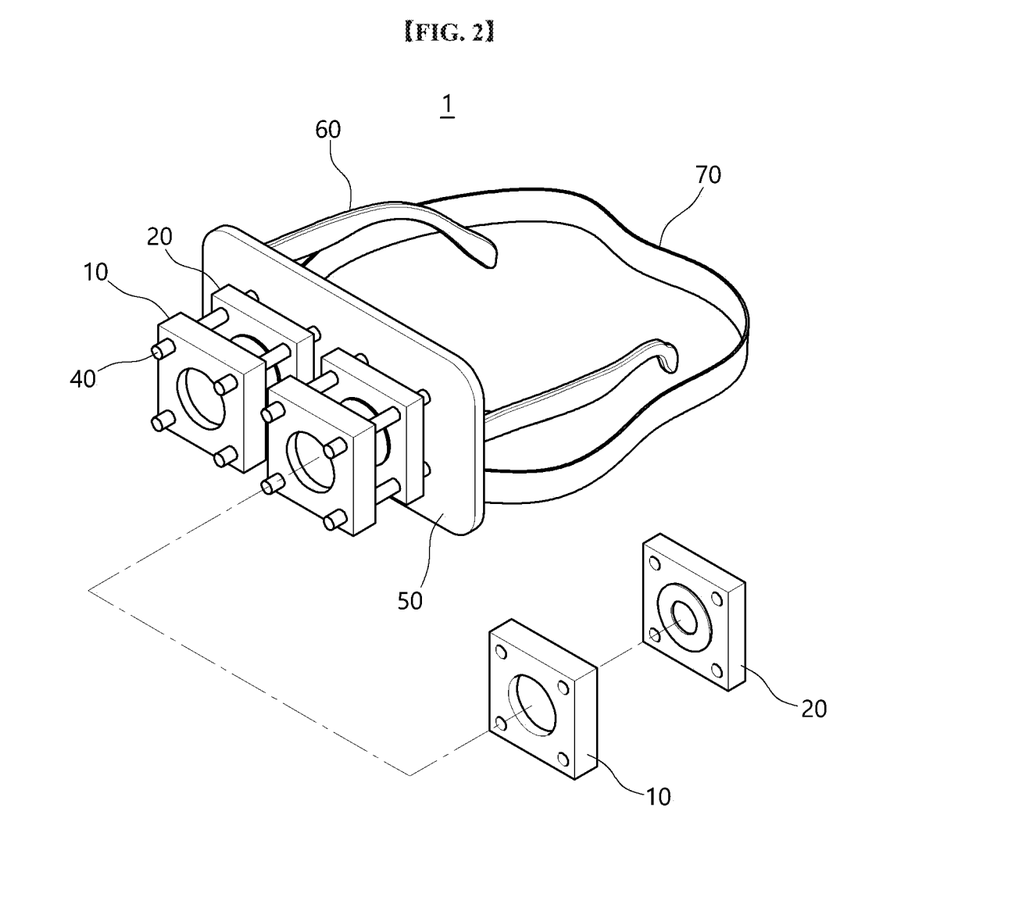
FIG. 2 is a perspective view of a wearable model eye apparatus according to an exemplary embodiment of the present invention.

Referring to FIGS. 1 and 2, the model eye apparatus 1 according to a first embodiment of the present invention includes a plurality of guide members 40, a frame 50, an intraocular lens (IOL) module 20, a minus lens module 10, and a wearing part.

Referring to FIGS. 1 and 2, the plurality of guide members 40 may be formed in a circular rod shape disposed parallel to each other. Here, it has a form in which two are arranged in parallel in the vertical direction.

In this case, the plurality of guide members 40 may be formed in a circular rod shape, a polygonal rod shape or a pipe shape. Here, it is preferable that the plurality of guide members 40 are installed in parallel to each other so that the guiding components have straightness.

Meanwhile, referring to FIG. 2, the frame 50 may be fixedly installed at the rear end of the plurality of guide members 40 to support the plurality of guide members 40 in a parallel state. Of course, a hole is formed in the frame 50 so that the wearer can secure a view.

In this case, the frame 50 may be made of a light metal material or synthetic resin, and may have its own rigidity so that the plurality of guide members 40 maintain a parallel state.

In this case, the frame 50 may be made of, for example, a flat plate shape, and may be formed with a groove for hanging the nose like glasses.

In this case, a cushion member for protecting the wearer may be provided on the rear surface of the frame 50. For example, if a cushioning part made of silicone is installed on the rear surface of the frame 50 and the cushioning part is in close contact with the wearer's face when the frame is worn, discomfort during wearing may be reduced to some extent.

Meanwhile, referring to FIGS. 1 and 2, the minus lens module 10 may be installed in front of the intraocular lens module 20 so as to move forward or backward by the guidance of the plurality of guide members 40, and a minus lens, that is, a concave lens, may be provided therein. Here, the minus lens module 10 can not only move forward or backward along the guide members 40 but also can be replaced with a minus lens module 10 having a different focus. That is, if it is moved linearly along the guide members 40, it is detachable and can be replaced with another module 10 or 20.

The intraocular lens module 20 may be installed in front of the frame 50 so as to move forward or backward by the guidance of the plurality of guide members 40, and an intraocular lens 26 may be installed therein. Here, the intraocular lens module 20 may not only move forward or backward along the guide members 40, but may also be replaced with another intraocular lens module 20. In addition, even if the intraocular lens 26 is the same, modules having different sizes of central holes 24*a* and 25*a* of the fixing adapters 24 and 25 for fixing the intraocular lens 26 from the front and back may be applied for replacement. This is because the size of the central holes 24*a* and 25*a* of the fixing adapters 24 and 25 is the same size or at least similar to that of the pupil, and the size of the light entering the eye through this is different. Such an intraocular lens module 20 may be appropriately selected by a doctor and applied while being replaced several times.

In this case, since the intraocular lens module 20 functions similarly to a magnifying glass, if only this is placed in front of the wearer's eye 30, the object only looks cloudy. Therefore, in order to solve this problem, according to an embodiment of the present invention, a minus lens is arranged in front of the intraocular lens module.

In this case, the intraocular lens may be a multifocal intraocular lens.

According to an embodiment of the present invention, the minus lens module 10 and the intraocular lens module 20 may be arranged in a line on the plurality of guide members 40.

In this case, bodies of the intraocular lens module 20 and the minus lens module 10 are, for example, made in a rectangular parallelepiped shape, a through-hole is formed in each corner portion thereof, and a plurality of guide members 40 are installed to penetrate through the through-holes 21*e*, thereby guiding each module 10 and 20 so as to have linear mobility. In this case, the intraocular lens module 20 and the minus lens module 10 may be disposed to contact each other, and may be moved along the guide members 40 at the same time to adjust the focus.

In this case, the focal length of the minus lens 10 may be shorter than the focal length of the intraocular lens module 20. That is, the absolute value of the focal length of the intraocular lens module 20 may be greater than the absolute value of the focal length of the minus lens. For example, the entire focal length of the intraocular lens module 20 may be 50 mm, and the focal length of the minus lens may be, for example, −40 mm to −50 mm.

The wearing part may be connected to the frame 50 such that the intraocular lens module 20 and the minus lens module 10 are arranged in a line in front of a wearer's eye 30 to be worn.

In this case, in the present embodiment, the wearing part may be a pair of glass frames 60 having one end connected to the frame 50 and the other end being able to be hung on the wearer's ear.

As another example, the wearing part may be in the form of a band 70 having both ends fixed to the frame 50 so as to pass around the wearer's head.

Of course, as shown in FIG. 2, both the glass frames 60 and the band 70 may be provided for the wearer's stable wearing.

Meanwhile, as another example, the wearing part may be formed in the form of a helmet for the wear's stable wearing, and may be formed in a form in which the frame 50 is fixed to the front of the helmet. In this case, the helmet may bear almost all of the load of the apparatus, thereby reducing the burden on the wearer.

Meanwhile, as another embodiment, it is possible to provide a model eye apparatus in the form of a telescope.

That is, the model eye apparatus may be fixed to any one of the inner shell and outer shell assembled so as to be able to move forward or backward with the inner and outer surfaces in close contact, and may include an intraocular lens module having an intraocular lens installed therein and a minus lens module installed, in front of the intraocular lens module, in the other one of the inner shell and outer shell so as to be able to move forward or backward and having a minus lens therein.

The model eye apparatus having such a configuration can adjust the focus by moving the inner shell and outer shell forward or backward, and the wearer can adjust the focus by placing the model eye apparatus in front of the eyes, and then experience the vision after surgery in advance by observing the surrounding objects.

Meanwhile, referring to FIGS. 3 to 7, the intraocular lens module 20 of the model eye apparatus may include a main body 21, an intraocular lens 26, window members 22 and 27, a fixing part, and an aqueous solution 23.

Referring to FIGS. 3 to 7, the main body 21 has a through-hole 21*a* formed in the center in the vertical direction.

In this case, the cross-section of the through-hole 21*a* may be formed in a circular shape.

In this case, the main body 21 may be formed in a substantially rectangular parallelepiped shape, and a through-hole may be provided at edges of the main body so that a plurality of guide members 40 may pass therethrough. In this case, the shape of the main body is not limited to a rectangular parallelepiped, and may have a cylindrical shape or a polyhedral shape depending on the shape.

In this case, an assembling jaw 21*b* having a reduced diameter may be formed at the lower end of the through-hole 21*a* of the main body 21, and a lower fixing adapter 24, an intraocular lens 26, and an upper fixing adapter 25 may be sequentially stacked over the assembling jaw 21*b*.

Figure 7:
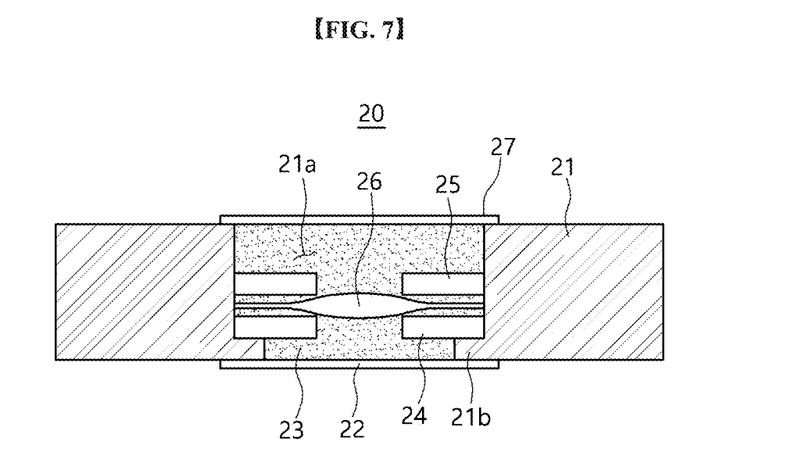

Referring to FIG. 7, the intraocular lens 26 is mounted in the horizontal direction so as to be fixed inside the through-hole 21*a* of the main body 21. The intraocular lens 26 is stably fixed inside the main body 21 by the upper and lower fixing adapters 24 and 25, thereby maintaining its state.

Referring to FIG. 7, the window members 22 and 27 are fixed at upper and lower ends so that the inside of the through-hole 21*a* of the main body 21 is sealed, and made of a transparent material.

In this case, the window members 22 and 27 may be manufactured using glass or synthetic resin panels. In addition, the window members 22 and 27 may be fixed to the main body 21 by being attached to the main body 21 by an adhesive.

Referring to FIG. 7, the fixing part fixes the position of the intraocular lens 26.

In this case, the fixing part is composed of an upper fixing adapter 25 and a lower fixing adapter 24, and the intraocular lens 26 is positioned therebetween to maintain a fixed state. That is, the intraocular lens 26 may be positioned between the upper and lower fixing adapters 24 and 25, but be indirectly fixed such that the intraocular lens 26 itself is not fixed to the main body 21 but the upper and lower fixing adapters 24 and 25 are fixed.

In this case, the upper and lower fixing adapters 24 and 25 may be in the form of a flat annular ring like a washer, and a method in which the upper fixing adapter 25 is fixed by tightening the headless bolt from the side, or a method of fixing an annular fixing bolt that is screwed onto the upper fixing adapter 25 may be applied. In addition to these fixing methods, by fixing the upper fixing adapter 25 in various ways, it is possible to stably fix the intraocular lens 26 at a predetermined position inside the main body 21.

Figure 14:
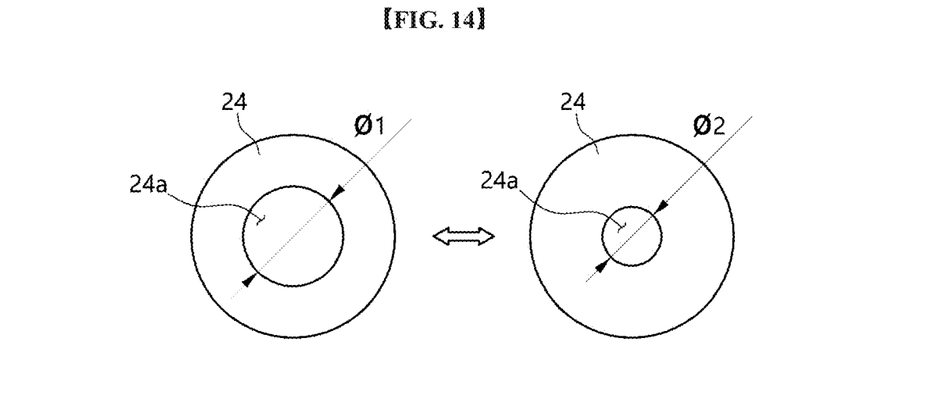
FIG. 14 is a front view of various types of fixing adapters, which are some components of a wearable model eye apparatus according to an exemplary embodiment of the present invention.

In this case, referring to FIG. 14, first, the central holes of the fixing adapters 24 and 25 have a size similar to that of the pupil, and the fixing adapters 24 and 25 having slightly different diameters $\Phi 1$ and $\Phi 2$ may be applied. The difference in the size of the central holes 24*a* and 25*a* corresponds to the pupil size of the patient, but allows the amount of light entering the eye to be adjusted. Therefore, the model eye apparatus can be worn in the most visible state while replacing the modules having the fixing adapters 24 and 25 of different sizes to the patient.

Meanwhile, referring to FIG. 7, the aqueous solution 23 may be water or physiological saline solution filled inside the through-hole 21*a*.

Figure 8:
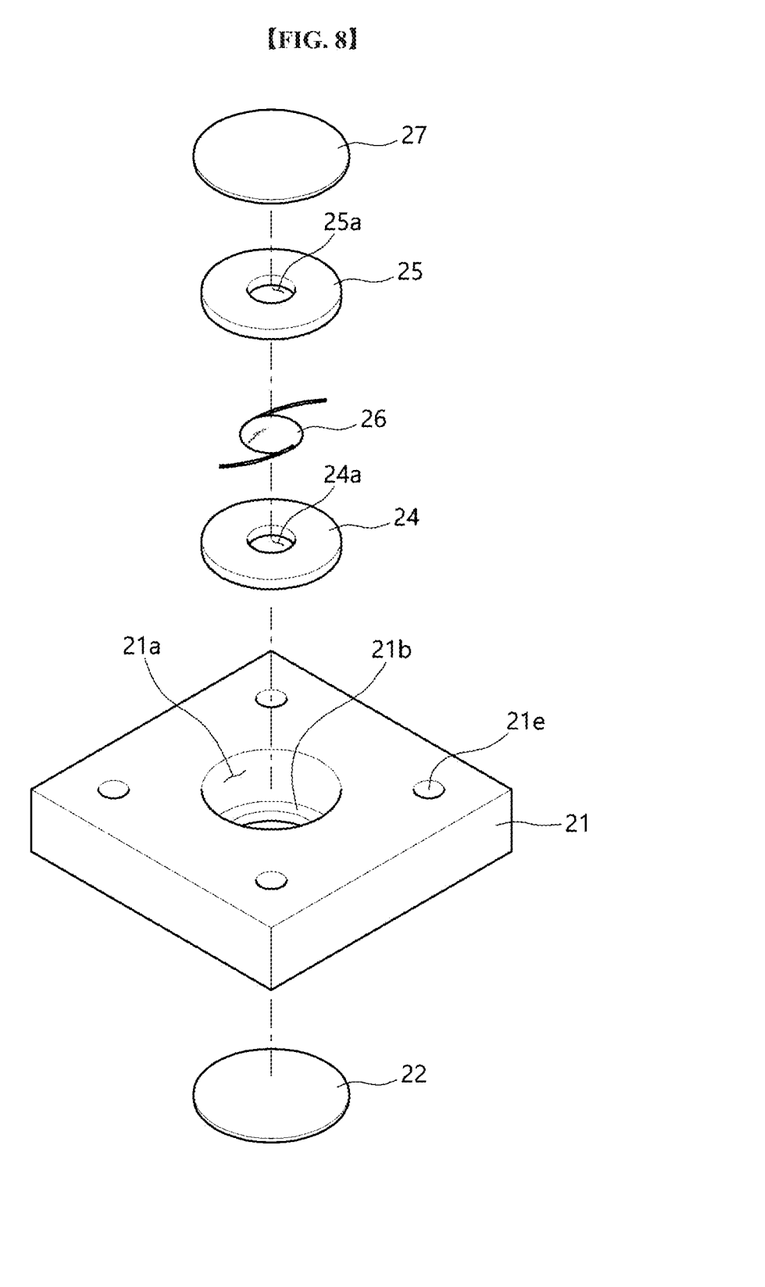
FIG. 8 is an exploded perspective view of an intraocular lens module according to an exemplary embodiment of the present invention.

The manufacturing process of the intraocular lens module 20 configured as described above is as follows with reference to FIGS. 3 to 8. Referring to FIG. 8, all components constituting the intraocular lens module are arranged.

Figure 3:
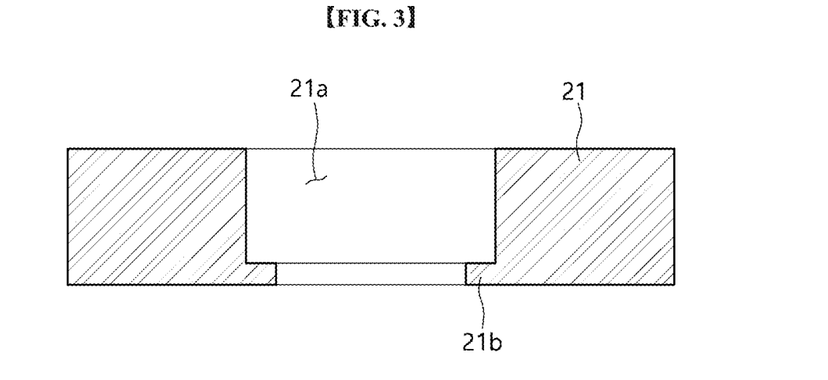
FIGS. 3 to 7 are cross-sectional views showing a manufacturing method of an intraocular lens module according to an exemplary embodiment of the present invention in order of manufacturing.

First, referring to FIG. 3, an intraocular lens main body 21 having a rectangular parallelepiped shape and having a through-hole 21*a* is prepared.

Figure 4:
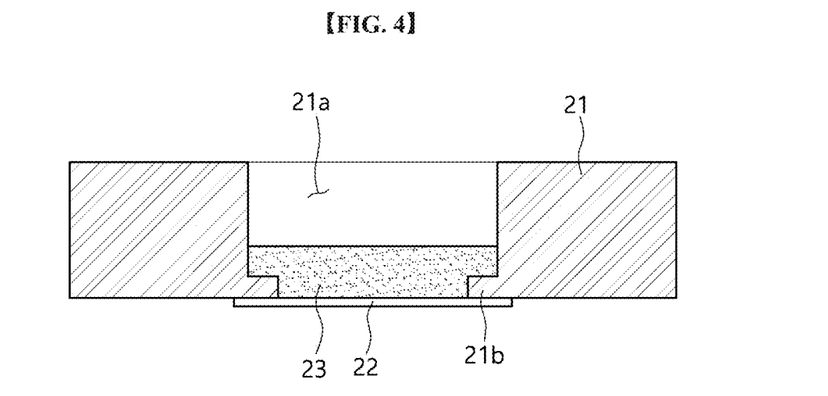

Referring to FIG. 4, a window member 22 is attached to a lower end of the intraocular lens main body 21 using an adhesive so as to be sealed, and a predetermined amount of physiological saline solution 23 is injected into a through-hole 21*a*.

Figure 5:
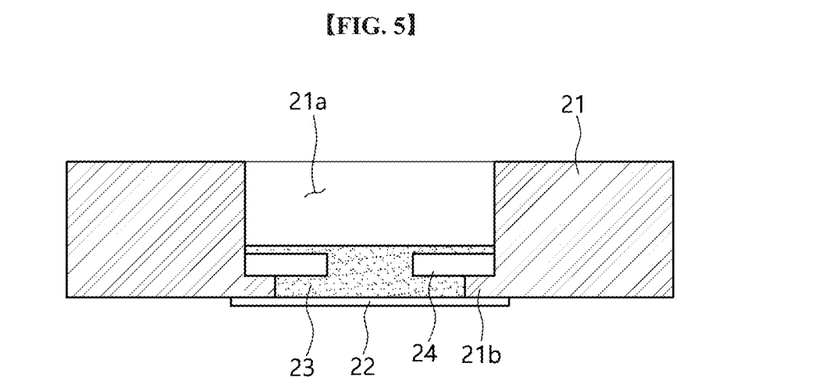

Referring to FIG. 5, a lower fixing adapter 24 is lowered to be positioned until it is caught on a latching jaw 21*b* of the through-hole 21*a*.

Figure 6:
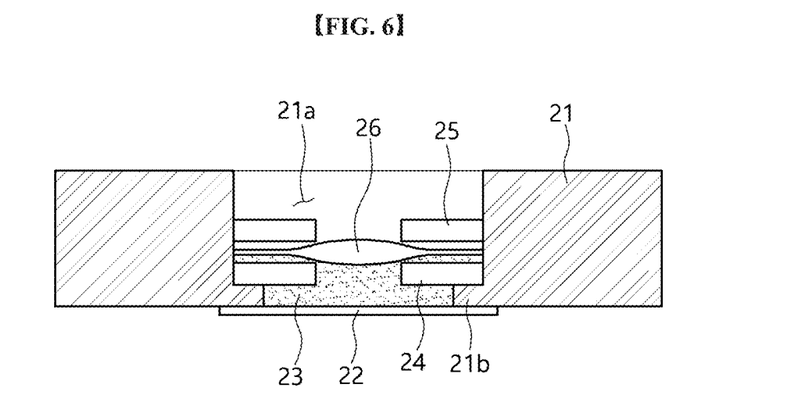

Referring to FIG. 6, an intraocular lens 26 is placed horizontally on the upper part of the lower fixing adapter 24, and in this state, an upper fixing adapter 25 is lowered on the upper part of the intraocular lens 26 to hold a position, and at the same time, the upper fixing adapter 25 is fixed by inserting a tool into the side of the main body 21 and fixing it with a headless bolt which is a fixing means.

Finally, referring to FIG. 7, the physiological saline solution is fully filled into the through-hole 21*a* and the window member 27 is attached to the upper surface of the main body 21 with an adhesive so that air bubbles are not generated as much as possible. Of course, the inside of the through-hole 21*a* is completely sealed.

The actual production of the movable model eye apparatus 1 according to the present invention configured as described above will be described, including the model name of each component.

The model eye apparatus comprises a minus lens, intraocular lens (IOL), and an intraocular lens module (IOL mount). For the minus lens, a lens with a focal length of 75 mm and a diameter of 0.5 inch was used. For the intraocular lens module mount, a window (thickness=1 mm, N-BK7 (WG11010)) with a diameter of 1 inch was glued to an SM05-Threaded 30 mm cage plate capable of mounting a 0.5 inch optic, and then filled with water. A 0.5 inch optic adapter was put into it, an intraocular lens (IOL) was put into it, and the same adapter (LMRA5, clear aperture 3.81 mm) was put into it and fixed with a retaining ring. Therefore, the diameter of the Iris is 3.81 mm. IOL centration was checked using a dissection microscope, and in particular, in the case of a diffractive IOL, it was confirmed that the diffractive ring was located at the center of the adapter aperture. It was filled with physiological saline solution and glued the same 1-inch window to the opposite side thereof. This model eye satisfies ISO 11979-2, 1999. The minus lens and IOL mount were constructed as a 30 mm cage system.

The intraocular lens module 20 is placed on the patient's eye side and the minus lens is placed on the opposite side, and the examiner adjusts the distance between the intraocular lens module and the minus lens so that objects at a distance of 6 m or more can be clearly seen. Through this apparatus, the patient can experience postsurgical vision by observing distant and near objects.

The intraocular lens used here may be a multifocal intraocular lens, but it is also applicable to other monofocal lenses and toric lenses.

As mentioned above, the apparatus can be made in the form of a telescope using only one eye or in the form of glasses.

Figure 9:
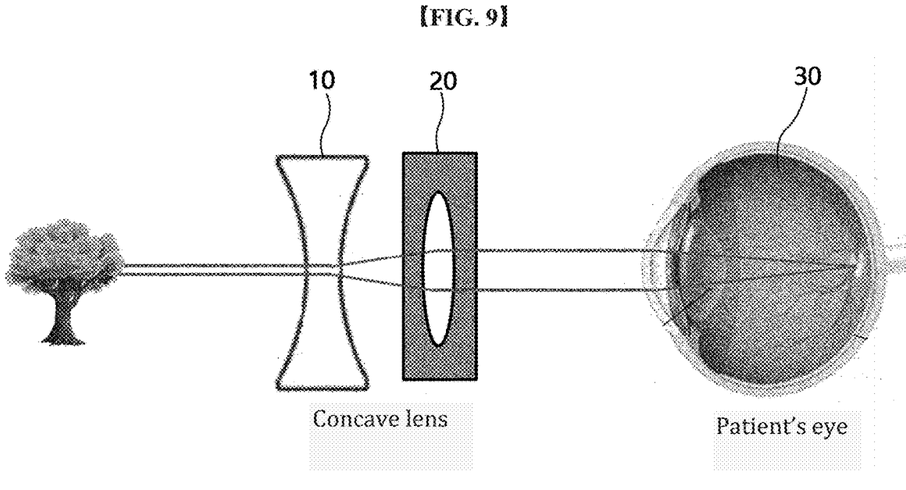
FIG. 9 is a mimetic diagram of an image forming on a person's eye through the passage of external light in a model eye apparatus according to an exemplary embodiment of the present invention.

FIG. 9 is a mimetic diagram of an image forming on a person's eye through the passage of external light in a model eye apparatus according to an exemplary embodiment of the present invention. The results actually photographed using the model eye apparatus 1 according to an embodiment of the present invention are shown in FIGS. 10 to 12.

Figure 10:
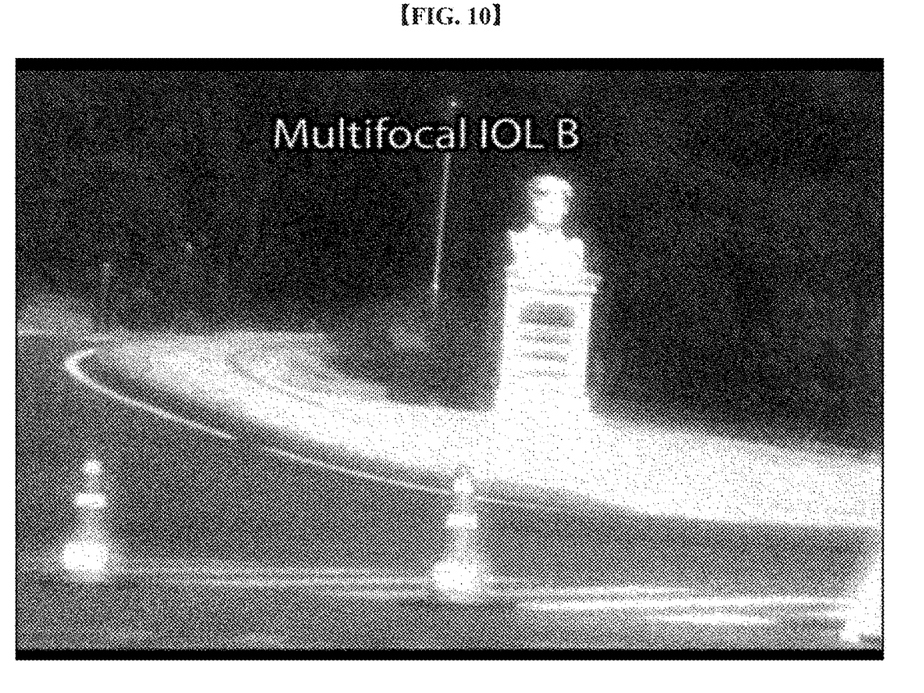
FIGS. 10 to 12 pictures taken of an image seen by a real person using a wearable model eye apparatus according to an exemplary embodiment of the present invention.
Figure 11:
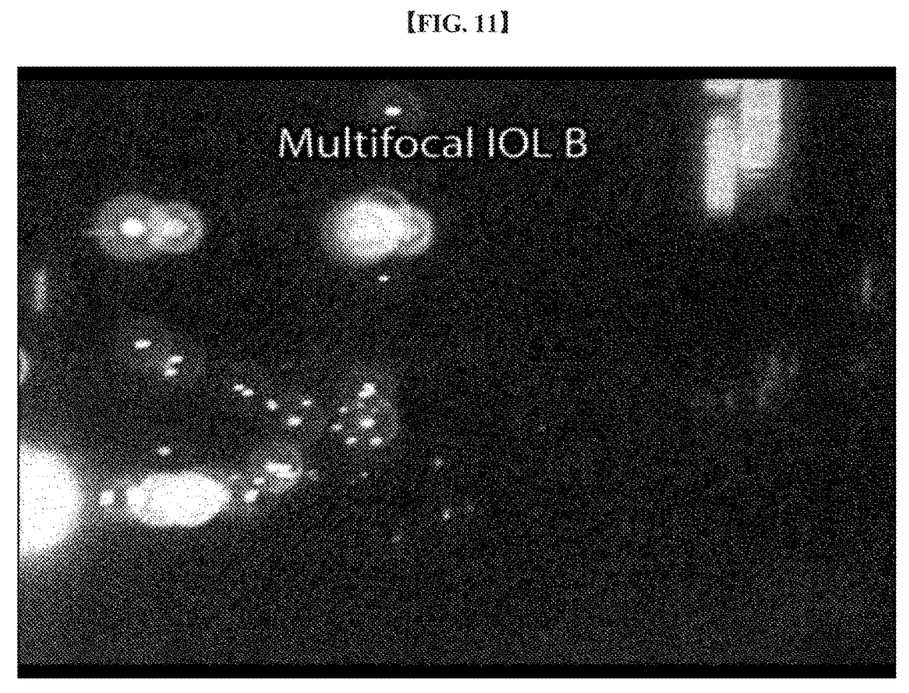
Figure 12:
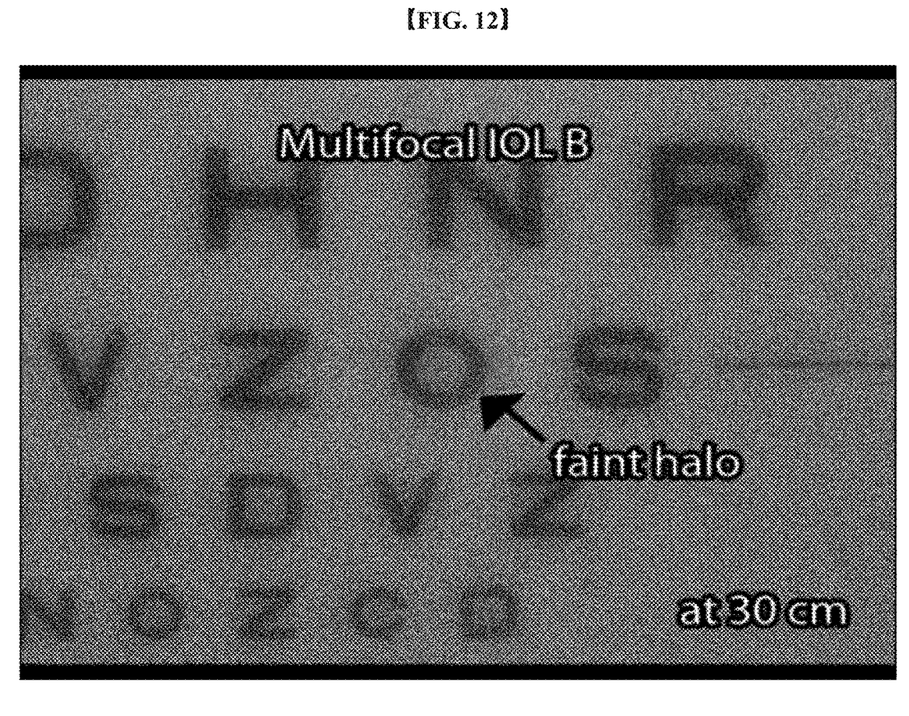

Since FIGS. 10 to 12 are images that a person sees when viewed using an actual multifocal intraocular lens, the images being photographed using a camera, by using the wearable model eye apparatus according to an embodiment of the present invention, it is possible to accurately and conveniently check how a person who has undergone multifocal intraocular lens surgery sees the real environment in a real environment such as outdoors.

Figure 13:
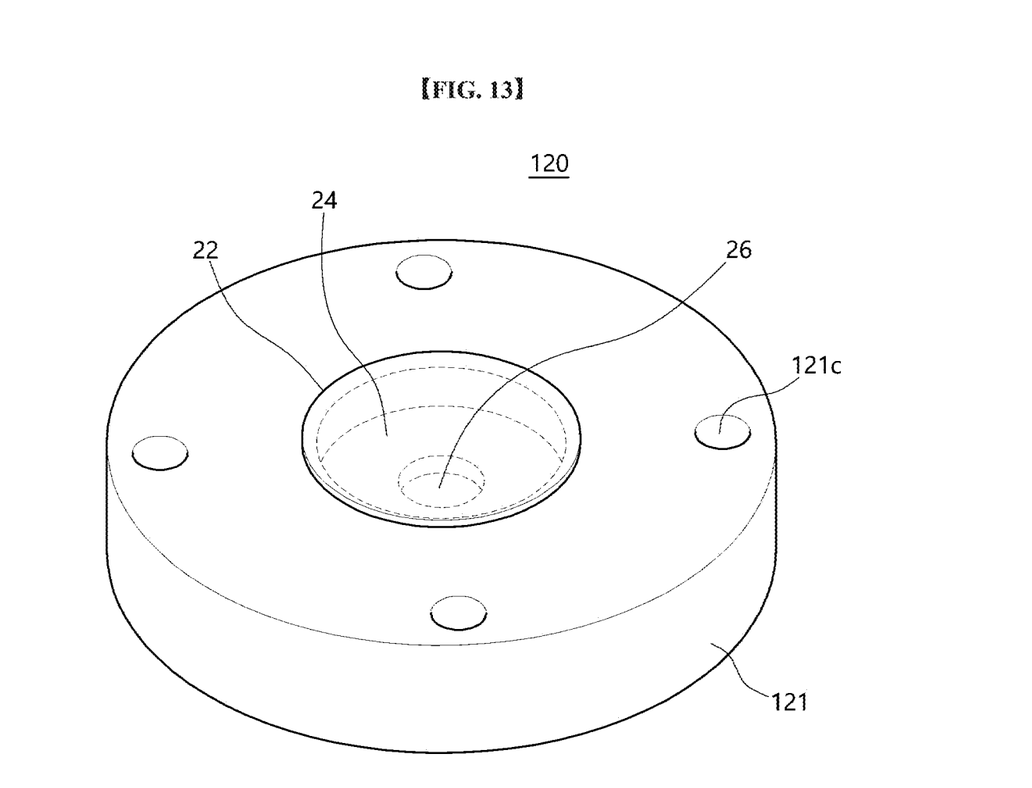
FIG. 13 is a perspective view of an intraocular lens module, which is a component of a wearable model eye apparatus according to another exemplary embodiment of the present invention.

Meanwhile, referring to FIG. 13, another form of the intraocular lens module 120 is illustrated. All other components other than the main body 121 are the same. The main body 121 is formed in a disk-shaped form rather than a hexahedral form. That is, the main body 121 has a circular shape on a plane, just as the components such as the window member 22 and the fixing adapter 24 are all circular shape on a plane. Of course, the through-hole 121c into which the guide member 40 is inserted is also formed at a corresponding position.

Although exemplary embodiments of the present invention have been described above, the spirit of the present invention is not limited to the embodiments set forth herein. Those of ordinary skill in the art who understand the spirit of the present invention may easily propose other embodiments through supplement, change, removal, addition, etc. of elements within the same spirit, but the embodiments will be also within the scope of the present invention.

INDUSTRIAL APPLICABILITY

The wearable model eye apparatus according to the present invention may be used in the medical field.

What is claimed is:

1. A wearable model eye apparatus, comprising:
a plurality of guide members arranged in parallel;
an intraocular lens module which is installed to be movable forward or backward by guidance of the plurality of guide members and has an intraocular lens installed therein; and
a minus lens module which is installed in front of the intraocular lens module to be movable forward or backward by guidance of the plurality of guide members and has a minus lens disposed therein,
wherein the intraocular lens module comprises:
a main body having a through-hole formed therein;
the intraocular lens mounted in a horizontal direction so as to be fixed inside the through-hole of the main body;
a window members fixed at upper and lower ends of the through-hole of the main body so that an inside of the through-hole of the main body is sealed, and made of a transparent material;
a pair of ring-shaped fixing adapters fixed to an assembling jaw formed inside the main body, wherein the intraocular lens is positioned fixedly between the pair of fixing adapters; and
an aqueous solution filled inside the through-hole.

2. The wearable model eye apparatus of claim 1, further comprising a frame fixedly installed at the rear end of the plurality of guide members to support the plurality of guide members in a parallel state.

3. The wearable model eye apparatus of claim 2, wherein a cushion member for protecting a wearer is provided on the rear surface of the frame.

4. The wearable model eye apparatus of claim 2, further comprising a wearing part connected to the frame such that the intraocular lens module and the minus lens module are arranged in a line in front of a wearer's eye to be worn.

5. The wearable model eye apparatus of claim 4, wherein the wearing part is a pair of glass frames having one end connected to the frame and the other end being able to be hung on the wearer's ear.

6. The wearable model eye apparatus of claim 4, wherein the wearing part is a band having both ends fixed to the frame so as to pass around the wearer's head.

7. The wearable model eye apparatus of claim 4, wherein the wearing part is made in the form of a helmet, and the frame is fixed to the front of the helmet.

8. The wearable model eye apparatus of claim 1, wherein a through-hole through which the plurality of guide members pass is formed in the main body of the intraocular lens module and the minus lens module so that the intraocular lens module and the minus lens module move forward or backward in the same direction.

9. The wearable model eye apparatus of claim 1, wherein bodies of the intraocular lens module and the minus lens module are made in a rectangular parallelepiped shape.

10. The wearable model eye apparatus of claim 1, wherein the minus lens module and the intraocular lens module are disposed to be in contact with each other.

11. The wearable model eye apparatus of claim 1, wherein the absolute value of the focal length of the intraocular lens module is greater than the absolute value of the focal length of the minus lens.

12. The wearable model eye apparatus of claim 1, wherein the intraocular lens is a multifocal intraocular lens.

13. The wearable model eye apparatus of claim 1, wherein the intraocular lens module and the minus lens module are detachably attached to the plurality of guide members so that they can be replaced with other modules.

14. The wearable model eye apparatus of claim 1, further comprising a plurality of replaceable intraocular lens modules in the guide member, wherein the size of the central holes formed in the fixing adapters of the plurality of intraocular lens modules is different from each other.

* * * * *